United States Patent

Giuliani et al.

(10) Patent No.: US 11,793,792 B2
(45) Date of Patent: Oct. 24, 2023

(54) COMPOSITION FOR PREVENTION AND TREATMENT OF HAIR GROWTH DISORDERS

(71) Applicant: GIULIANI S.P.A., Milan (IT)

(72) Inventors: Giammaria Giuliani, Montagnola (CH); Barbara Marzani, Carbonara al Ticino (IT); Daniela Pinto, Milan (IT); Sergio Baroni, Villa D'Adda (IT); Ralf Paus, Hamburg (DE); Nathan Hawkshaw, Manchester (GB)

(73) Assignee: GIULIANI S.P.A., Milan (IT)

( * ) Notice: Subject to any disclaimer, the term of this patent is extended or adjusted under 35 U.S.C. 154(b) by 281 days.

(21) Appl. No.: 16/969,246

(22) PCT Filed: Feb. 13, 2019

(86) PCT No.: PCT/EP2019/053591
§ 371 (c)(1),
(2) Date: Aug. 12, 2020

(87) PCT Pub. No.: WO2019/158607
PCT Pub. Date: Aug. 22, 2019

(65) Prior Publication Data
US 2021/0000801 A1 Jan. 7, 2021

(30) Foreign Application Priority Data
Feb. 13, 2018 (IT) .......... 102018000002630

(51) Int. Cl.
*A61K 31/427* (2006.01)
*A61P 17/14* (2006.01)
*A61K 8/49* (2006.01)
*A61Q 7/00* (2006.01)

(52) U.S. Cl.
CPC .......... *A61K 31/427* (2013.01); *A61K 8/4986* (2013.01); *A61P 17/14* (2018.01); *A61Q 7/00* (2013.01)

(58) Field of Classification Search
CPC ..... A61K 31/427; A61K 8/4986; A61P 17/14; A61Q 7/00
See application file for complete search history.

(56) References Cited

U.S. PATENT DOCUMENTS

2006/0270720 A1\* 11/2006 Gopalsamy ............. A61P 19/00
514/369

FOREIGN PATENT DOCUMENTS

| EP | 1775294 A1 | 4/2007 |
| JP | 2017524724 A | 8/2017 |
| WO | 2006/124887 A1 | 11/2006 |

OTHER PUBLICATIONS

Shi et al., "Identification of iminooxothiazolidines as secreted frizzled related protein-1 inhibitors", 2009, Bioorganic & Medicinal Chemistry Letters, vol. 19, pp. 6337-6339. (Year: 2009).\*
International Search Report and Written Opinion for corresponding Application No. PCT/EP2019/053591 (dated Apr. 29, 2019).
Shi et al., "Identification of Iminooxothiazolidines as Secreted Frizzled Related Protein-1 Inhibitors," Bioorg. Med. Chem. Letts. 19(22):6337-6339 (2009).
Katzman et al., "A Novel Class of Negative Allosteric Modulators of NMDA Receptor Function," Bioorg. Med. Chem. Letts. 25(23): 5583-5588 (2015).

\* cited by examiner

*Primary Examiner* — Michael B. Pallay
(74) *Attorney, Agent, or Firm* — Troutman Pepper Hamilton Sanders LLP (Rochester)

(57) ABSTRACT

The present invention relates to the use of iminooxothiazolidine derivatives for preventing or treating hair growth disorders. The iminooxothiazolidine derivatives may be formulated as compositions suitable for either the systemic administration or the local application to the scalp.

9 Claims, 2 Drawing Sheets

COMPOSITION FOR PREVENTION AND TREATMENT OF HAIR GROWTH DISORDERS

This application is a national stage application under 35 U.S.C. § 371 of PCT Application No. PCT/EP2019/053591, filed Feb. 13, 2019, which claims priority benefit of Italy Application No. 102018000002630, filed Feb. 13, 2018, which are hereby incorporated by reference in their entirety.

FIELD OF THE INVENTION

The present invention relates to a composition for treating hair growth disorders. Specifically, the present invention originates in the cosmetic/trichological and nutritional fields and concerns formulations or supplements suitable for stimulating the physiological growth of hair and preventing or treating hair loss.

PRIOR ART

Hairs have a protecting role and are considered as a skin annex along with sebaceous glands, sudoriferous glands and nails.

The life cycle of the hair bulb includes three main phases: a growth phase known as anagen, an involution phase known as catagen and a rest phase known as telogen.

Hair on the scalp is produced by hair follicle, a mammalian skin organ. Hair follicles do not continuously produce hair. They cycle through a growth stage that can last two or more years and regress to a resting stage for up to two months before starting to grow a new hair fiber again.

The biological phases of this phenomenon reside in the capability of stem cells of the bulb to leave, at alternating steps, their state of quiescence. During the bulb growth and hair production phase the proliferation, differentiation and survival activities are prevailing which are regulated by growth factors. The regression phase, on the contrary, is characterized by the activation of molecular pathways that induce apoptosis in bulb cells.

In the anagen phase, the dermal papilla generates chemical signals that activate and instruct the stem cells of the bulge which by migrating to the base of the follicle form the hair matrix. With this "migration" the stem cells of the bulge create a "path" of cells which will give rise to the outer root sheath or ORS.

In response to further signals by the dermal papilla, the matrix cells, which derive from stem cells, proliferate and start the differentiation process, by moving upwards to form the shaft and inner sheath of the hair follicle.

The start of the catagen phase is characterized by the end of cell proliferation and the apoptosis of matrix cells. During catagen the dermal papilla migrates towards the lowermost portion of the bulge. This close proximity of the papilla to the bulge is believed to be essential for initiating another hair production cycle. This enables interaction/activation of bulge cells at rest and a new cycle of hair growth.

Upon catagen/telogen transition, some cells of the bulge migrate to meet the papilla, generating the hair germ.

Hair in telogen contains a cell population at its base, which is in fact called hair germ, located in close proximity to the dermal papilla. The hair germ is activated to proliferate towards the end of the telogen phase, even before the bulge, to form, by surrounding the papilla, the matrix of the new bulb.

Different factors, among which stress, the lack of nutrients and ageing, negatively affect the life cycle of the hair bulb, determining a reduction of the number of hairs and their thinning.

Hair growth disorders are very common in particular in the male population. If the role of hair is considered in social relations, hair loss may be hard to face for many people.

One of the more widely spread hair disorder is represented by alopecia, a disorder in the hair growth which may be caused by different factors from genetics to environmental. The degree and pattern of alopecia may vary, however one of the most common alopecia form is represented by androgenetic alopecia (AGA). Alopecia forms other than androgenetic alopecia include telogen effluvium, alopecia areata, ringworm, scarring alopecia, and hair loss due to cosmetic overprocessing.

In individuals affected by androgenic alopecia (AGA), the follicles that form at the start of the new anagen phase decrease in size with the passing of time (miniaturisation), leading, as time proceeds, to the formation of a hair that is smaller than the previous one. The result is the formation of a microscopic hair.

Dermatologists classify alopecias by subdividing them into the cicatricial and noncicatricial categories. Some types of alopecia such as lichen planopilaris, discoid lupus erythematous and graft-versus-host-disease are associated with the bulge follicle stem cell destruction and with permanent hair loss. In the reversible types of alopecia such as in alopecia areata, inflammation affects the follicle progenitor cells, but spares the stem cells thereof. In these diseases, regrowth takes place on elimination of the inflammation and on the consequent regeneration of the hair follicle starting from undamaged stem cells.

In individuals suffering from androgenetic alopecia (AGA), over time the follicles, which are formed again at the beginning of the new anagen phase, become smaller in size, leading to the formation of hair with smaller diameter as compared to the initial diameter. As a consequence, the formation of microscopic hair occurs. It was observed that although the follicles of scalp atrophy, there still remains a supply of stem cells which convert to progenitor cells, even though to a lesser extent as compared to the scalp in physiological conditions.

At present many options for the treatment of hair growth disorders, included alopecia, are available.

A first line of treatments includes the topical application and/or the administration of formulations for preventing and treating hair growth disorders. Most of the hair formulations available on the market target hair bulbs and act on scalp metabolism, feeding, oxygenation and microcirculation improving the conditions contributing to a physiological growth of hair.

Typically, these trichological products incorporate cosmetic ingredients for restoring skin and the conditions suitable for promoting hair growth.

A large number of trichological products contain antioxidant substances, such as vitamin E, glycosaminoglycan such as hyaluronic acid, and vitamins such as vitamin A and vitamins of the B group or derivatives thereof such as niacin or nicotinamide adenine dinucleotide (NAD).

However, in many cases the application of trichological compositions containing the above and other ingredients to the scalp or the administration of nutritional formulations have shown a poor effect on the stimulation of hair growth.

Trichological products containing pharmacologically active substances as trichological ingredients have shown a superior activity with respect to the cosmetic/trichological formulations.

Amongst these pharmaceutical products, the formulations containing minoxidil, a pharmacologically active ingredient provided with vasodilator activity, are well known. These products are usually formulated as alcoholic solutions for topical application.

Other products used for treating hair disorders include pharmaceutical compositions containing finasteride, an hormonal substance. These products inhibit the Type II 5-alpha-reductase, an enzyme converting testosterone into dihydrotestosterone (DHT), an hormone which shrinks or miniaturizes hair follicles and leads to baldness when the secretion exceeds the physiological production.

However, the use of minoxidil and finasteride are not free from drawbacks. Specifically, the topical application of minoxidil may lead to local side effects such as skin rashes, local inflammations, and to general drawback such as headache, hirsutism, while the oral administration of finasteride may results in hormonal dysfunctions.

Accordingly, there is still a need for obtaining alternative remedies for treating hair growth disorders which are effective and possibly free of serious side effects.

One of the aims of the present invention consists in providing new uses in the trichological field for already known compounds.

Another aim resides in providing a composition for stimulating the physiological hair growth in subjects affected by baldness or thinning of the hair.

Another object of the invention is to provide a composition both for cosmetic and pharmaceutical use which may be administered either through the local or the systemic route of administration.

SUMMARY OF THE INVENTION

In general terms, the present invention provides new uses in the cosmetic and trichological field for certain iminooxothiazolidine derivatives.

In accordance with certain aspects, the inventors have unexpectedly found that certain iminooxothiazolidine derivatives which are known compounds for use in the treatment of osteoporosis or other bone related disorders, stimulates the hair growth when are applied locally on the scalp or when are systematically administered.

In accordance with a first aspect the present invention thus provides the cosmetic, non therapeutical use of iminooxothiazolidine derivatives of formula (I)

wherein
$R_1$ is H, linear or branched $C_1$-$C_6$ alkyl, cycloalkyl, phenyl, —$CH_2$—NH-phenyl;
$R_2$ is H, linear or branched $C_1$-$C_6$ alkyl, halogen, phenyl;
$R_3$ is COO($C_1$-$C_6$)alkyl, CONR$_4$R$_5$ wherein $R_4$ and $R_5$ individually are H or $C_1$-$C_6$ alkyl, or $R_1$ and $R_2$ together form a $C_5$-$C_7$ cycloalkyl fused with the thiophene ring for treating hair growth disorders.

In accordance with a second aspect the present invention provides iminooxothiazolidine derivatives of formula (I)

wherein
$R_1$ is H, linear or branched $C_1$-$C_6$ alkyl, cycloalkyl, phenyl, —$CH_2$—NH-phenyl;
$R_2$ is H, linear or branched $C_1$-$C_6$ alkyl, halogen, phenyl;
$R_3$ is COO($C_1$-$C_6$) alkyl, CONR$_4$R$_5$ wherein $R_4$ and $R_5$ individually are H or $C_1$-$C_6$ alkyl, or $R_1$ and $R_2$ together form a $C_5$-$C_7$ cycloalkyl fused with the thiophene ring for use in the treatment of a hair growth disorder or affection.

In accordance with a third aspect, the present invention provides the cosmetic use of a composition comprising a compound of formula I and a physiologically acceptable carrier for stimulating the physiological growth of hair.

In accordance with some embodiments, the composition of the invention is a cosmetic composition suitable for topical application.

In accordance with certain embodiments, the composition for cosmetic use is a cosmetic composition, a food supplement or a nutraceutical composition which may be introduced into the dietary regimen of a subject suffering of a trichological disorder such as hair loss, hair thickening or discoloration.

The inventors observed that the iminooxothiazolidine derivatives of formula (I) when administered through the topical or systemic route to a subject suffering from hair thinning or hair loss, give a progressive thickening of thinner areas of the scalp.

In accordance with certain aspects, a composition is provided containing the iminooxothiazolidine derivatives of formula (I) and a physiologically acceptable carrier for use in the treatment of hair growth disorders.

According to certain embodiments, the composition of the present invention is a pharmaceutical composition.

Typically, the composition of the invention contains a trichologically or pharmaceutically active amount of the iminooxothiazolidine derivatives of formula (I).

Certain aspects and advantages of the invention are further described with reference to the appended drawing.

DETAILED DESCRIPTION OF THE INVENTION

In accordance with certain aspects of the invention, the inventors found that a selected class of iminooxothiazolidine derivatives of formula (I) found application in the trichological field and are useful in the prevention or treatment of hair growth disorders.

The compounds of formula (I) find application in the prevention or treatment of trichological or hair growth disorders.

The Applicant discovered that compounds of formula (I) exert a trichological activity and stimulates the activity of follicle cells and of quiescent hair bulbs of the scalp. These activities activate the life cycle of hair follicles promoting the hair growth.

In accordance with a first aspect the present invention thus provides the cosmetic/non therapeutical use of iminooxothiazolidine compounds of formula (I)

(I)

wherein
$R_1$ is H, linear or branched $C_1$-$C_6$ alkyl preferably $C_1$-$C_3$ alkyl, ($C_3$-$C_6$)cycloalkyl, phenyl, —$CH_2$—NH-phenyl;
$R_2$ is H, linear or branched $C_1$-$C_6$ alkyl preferably $C_1$-$C_3$ alkyl, halogen, phenyl;
$R_3$ is COO($C_1$-$C_6$) alkyl preferably COO($C_1$-$C_3$)alkyl, CONR$_4$R$_5$ wherein $R_4$ and $R_5$ individually are H or $C_1$-$C_6$ alkyl preferably $C_1$-$C_3$ alkyl, or $R_1$ and $R_2$ together form a $C_5$-$C_7$ cycloalkyl fused with the thiophene ring for promoting hair growth or preventing or slow down hair loss.

A preferred halogen is Br.

In accordance with certain embodiments $R_1$ is H or $C_1$-$C_3$ alkyl, preferably methyl;
$R_2$ is H, alogen preferably Br or $C_1$-$C_3$ alkyl preferably $CH_3$ and $R_3$ is COO($C_1$-$C_3$) alkyl preferably a methyl or ethyl ester.

In certain embodiments $R_1$ is H or $C_1$-$C_3$ alkyl,
$R_2$ is H or halogen, preferably Br,
$R_3$ is COOCH$_3$ or COOCH$_2$CH$_3$.

Preferred compounds of formula (I) have the following substituent groups:
$R_1$ is methyl, $R_2$ is Br and $R_3$ is COOethyl;
$R_1$ is methyl, $R_2$ is H and $R_3$ is COOethyl
$R_1$ is H, $R_2$ is H and $R_3$ is COOmethyl
$R_1$ is —$CH_2$—NH-phenyl, $R_2$ is Br and $R_3$ is COOethyl.

In accordance with certain embodiments the compounds of formula (I) reported in the following Table 1 are provided, preferably compounds C1, C5, C7, C17 which are more active, especially compounds C1 and C5.

Most preferred compounds are 2-(2-(2-Imino-4-oxo-thiazolidin-5-yl)-acetylamino)-4,5-dimethyl-thiophene-3-carboxylic acid methyl ester and 2-(2-(2-Imino-4-oxo-thiazolidin-5-yl)-acetylamino)-4,5-dimethyl-thiophene-3-carboxylic acid ethyl ester.

According to the invention the compounds of formula (I) are useful in the cosmetic field for the prevention or treatment of hair loss, hair fall, in the prevention of graying or in the cosmetic treatment of gray hairs. The compounds of formula (I) are also useful for improving an aesthetic aspect of the hair such as hair pigmentation.

Typically, the compounds of formula (I) stimulates the physiological growth of hair and the thickening of the hair.

In accordance with a second aspect the present invention concerns pharmaceutical uses of the compounds of formula (I) for treating hair growth disorders/affections.

In accordance with this latter aspect, iminooxothiazolidine compounds of formula (I) are provided (I)

wherein
$R_1$ is H, linear or branched $C_1$-$C_6$ alkyl preferably $C_1$-$C_3$ alkyl, ($C_3$-$C_6$)cycloalkyl, phenyl, —$CH_2$—NH-phenyl;
$R_2$ is H, linear or branched $C_1$-$C_6$ alkyl preferably $C_1$-$C_3$ alkyl, halogen, phenyl;
$R_3$ is COO($C_1$-$C_6$) alkyl preferably COO($C_1$-$C_3$)alkyl, CONR$_4$R$_5$ wherein $R_4$ and $R_5$ individually are H or $C_1$-$C_6$ alkyl, preferably $C_1$-$C_3$ alkyl, or $R_1$ and $R_2$ together form a $C_5$-$C_7$ cycloalkyl fused with the thiophene ring for use in the treatment of hair growth disorders or affections.

A preferred halogen is Br.

The hair growth disorders or affections which may be treated according to this aspect of the invention include alopecia and telogen effluvium, disorders affecting subjects of male and female gender. The composition is also suitable for treating or preventing female pattern, baldness, or androgenetic alopecia.

Iminooxothiazolidine compounds and method for preparation thereof are disclosed in the International patent application WO 2006124887 to Wyeth Corp., USA.

In accordance with a third aspect, the present invention provides the cosmetic, non-therapeutic, use of a composition comprising an iminooxothiazolidine compound of formula (I) according to any one of the embodiments described hereinabove, and a physiologically acceptable carrier for stimulating the physiological growth of hair. The composition of the invention is effective in preventing and/or treating forms of baldness or hair thinning as described above.

The composition for cosmetic use is either for the local or systemic administration. In accordance with some embodiments, the composition for oral administration is a functional food, a nutraceutical composition, a dietary product, a food supplement or a nutritional product or a medical device.

Functional food means any modified food or food ingredient which may provide a benefit or protection against a drawback or a physiological condition, besides the traditional nutrients it contains.

Nutraceutical product means a product isolated or purified from edible substances. A nutraceutical product is such when it shows to have a physiological advantage or to provide protection against a drawback or physiological disorder.

Independently from the routes of administration, the cosmetic composition increases the viability of follicle cells during the anagen phase and activates the quiescent cells of the scalp by stimulating the metabolism of follicles and the growth of new hair.

In accordance with a fourth aspect, a composition is provided containing an iminooxothiazolidine compound of formula (I) according to any one of the embodiments described hereinabove, and a pharmaceutically acceptable carrier for use in the treatment of hair growth disorders.

Example of hair growth disorders treated by these compositions include alopecia and telogen effluvium. Typically, these compositions are formulated as pharmaceutical compositions.

The amount of active compounds of formula (I) in compositions for cosmetic/pharmaceutical/nutritional uses is such that a prophylactic or therapeutically effective dosage is obtained.

In accordance with certain embodiments the composition for both cosmetic and medical uses may contain an iminooxothiazolidine compound of formula (I) in an amount of 0,0001 to 15% by weight, 0,001 to 10% by weight or 0.1 to 3% by weight.

In certain embodiments, the composition of the invention may further comprise one or more additional ingredients having a trichological activity.

The amount administered and the frequency of administration of the composition will depend on the type and severity of the trichological condition to be treated.

In certain embodiments the compositions for both cosmetic and therapeutical uses further includes additional ingredients such as vitamins, for example vitamin A, vitamin C, vitamins of the B group, niacin.

In accordance with some embodiments the composition of the invention further contains an amino acid, in particular a sulfur-containing amino acid, such as L-cysteine or L-Methionine, especially for formulations for the oral administration.

In accordance with some embodiments the composition of the invention also includes one or micro micronutrients and/or minerals or micronutrients such as Mg, Zn, Ca, Fe, Cr, Se, and others, especially for formulations for the oral administration.

In certain embodiments the composition may further contain additional substances such as folic acid, calcium pantothenate, mucopolysaccharides such as hyaluronic acid, or soy derivatives such as soy isoflavones.

In some embodiments the composition of the invention for both cosmetic and medical uses comprises a physiologically and/or pharmaceutically acceptable carrier, diluent or excipient.

Typically, the physiologically acceptable carrier of the composition of the invention is an excipient, carrier or diluent suitable for topical application and/or systemic administration. Physiologically and pharmaceutically carriers may be the same carriers.

Within the scope of the present document, the term "carrier" relates to an excipient, carrier, diluent or adjuvant that may be present in the composition of the invention. Any carrier and/or excipient suitable for the form of preparation desired for administration is contemplated in the uses of the vegetal extract or herein described active ingredients present therein.

Typically, a suitable carrier is a physiologically, edible or pharmaceutically acceptable carrier.

Typically, the compositions for oral administration may contain one or more edible carriers.

For purposes of the present application, the term "edible" is intended to mean food grade materials which are approved by regulatory authorities for use in nutritional or food applications. The term "trichological disorder" means any conditions where there is a change in the physiological conditions of hair, especially a change in an aesthetic aspect of hair. The compositions of the present invention encompass any compositions made by admixing the association of a compound of formula (I) and a physiologically acceptable carrier. Such compositions are suitable for nutritional, pharmaceutical or dietetic use in a mammal, specifically human beings.

The carrier may take a wide variety of suitable forms depending on the form of preparation desired for both the systemic or local administration.

Accordingly, the physiologically and/or pharmaceutically acceptable carrier, diluent or excipient may be selected based on the route of administration for which the composition is intended.

The compositions for oral administration may be in the solid or liquid form.

Typical compositions in the solid form comprise tablets, capsules, powders, granules, pills. If desired, the tablets may be coated with a suitable polymeric agent or agent for obtaining the sustained/prolonged release by conventional techniques.

Exemplary excipients used in the solid forms include cellulose derivatives such as hydroxymethyl cellulose, hydroxypropyl methylcellulose, methylcellulose, hydroxypropyl cellulose, hydroxyethyl cellulose, carboxyethyl cellulose, ethylhydroxyethyl cellulose, cellulose acetate butyrate, cellulose acetate phthalate, and mixtures thereof.

Further examples of suitable excipients include polymers of the class of lactams, typically pyrrolidone and derivatives thereof, such as polyvinylpyrrolidone, polyvinylpolypyrrolidone and mixtures thereof, inorganic salts for example calcium or dicalcium phosphate, lubricants for example magnesium stearate, triacylglycerols and mixtures thereof.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, saccharin or other sweeteners. When a dosage unit form is a capsule, it may contain, in addition to materials of the above type, a liquid carrier such as a fatty oil.

In certain embodiments, the composition of the invention further includes one or more additional components, such as additives, fillers, stabilizers, emulsifying, texturizing, filmogenic, plasticizing, wetting agents, and thickeners.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor. To prevent breakdown during transit through the upper portion of the gastrointestinal tract, the composition may be an enteric coated formulation.

Typical compositions in the liquid form for oral administration include solutions, suspensions, syrups, emulsions, gels.

In these forms administrations, suitable carriers include water, glycols, or oil-in-water or water-in-oil emulsions containing the compounds of formula (I) dispersed therein.

In certain embodiments the composition is administered by the systemic route, especially by injection. In the composition for injection purposes the compound of formula (I)

or pharmaceutically salts thereof are dissolved in a pharmaceutically acceptable solvent such as water for injection. The composition for injection purposes may further contain at least one of a buffer/buffer system, preservatives, co-solvents or additives.

In some embodiments, the route of administration of the composition of the invention is topical. The compositions for topical administration may be in the solid, semi-liquid or liquid form. Typically, the topical composition is applied onto the skin, and in particular onto the scalp in an effective amount.

For example, for the cosmetic uses, a cosmetically active amount of a composition of the invention may be applied directly to the scalp once or multiple times a day conveniently for cycles lasting 2-3 months, alternating with rest periods.

The composition for topical application may be in the solid, semi-solid or fluid form. Suitable formulations in the solid form include creams, gels, pastes, ointments.

In other embodiments the formulation for local administration is in the fluid form, for example in the form of lotions, gels, shampoos, suspensions, emulsions.

In the case of formulations in the fluid or semi-fluid form, the compound of formula (I) may be diluted in a carrier in the physiologically acceptable liquid form such as water, alcohol, hydroalcoholic or glyceric solution or mixed with other liquids suitable for local application.

In the form of a solution, suspension or dispersion, the composition of the invention may contain from around 1-99.9% of a liquid such as water optionally mixed with an alcohol. In some embodiments, water is present in an amount of between 5-95%. In other embodiments, water is present in an amount of between 10-90% by weight.

A typical composition for topical use is a hydro alcoholic solution containing a compound of formula (I) dissolved therein.

By way of example, the compositions of the invention in liquid form can be prepared by dissolving the water soluble components and the remaining components in alcohol to then reunite the various fractions under agitation. The resulting mixture can then be buffered to reach a pH interval conveniently selected between 5 and 7 so as to be compatible with the pH of the scalp to then be filtered and packaged in suitable containers such as bottles or vials.

In certain embodiments the composition of the invention is in the form of a lotion for external use.

Typically, the active compounds of formula (I) of the pharmaceutical compositions are formulated in dosage units. The dosage unit may contain from 0.1 to 1000 mg of active ingredient per dosage unit for daily administration.

In some embodiments, the amounts effective for formulation will depend on the severity of the disorder or condition to be treated. In some embodiments, the dose is in the range from 0.001% by weight to about 60% by weight of the formulation.

In accordance with certain aspects the invention relates to compositions for topical use which are useful in the stimulation of hair follicles, with a resulting benefit of treating hair growth disorders, such as alopecia, in females in particular. Methods of treatment of relevant populations are also a feature of the invention.

According to another aspect of the invention, there is provided a method of cosmetic treatment which comprises the application to the scalp of an effective amount of a composition of the type described previously.

For example, for local uses, a cosmetically or pharmaceutically active amount of the composition of the invention is applied directly to the scalp one or more times daily, conveniently for cycles having a duration of 2-3 months alternating with periods of rest.

The following examples are provided merely for illustrating the present invention and are not to be intended as limiting the scope of protection as results from the appended claims.

EXAMPLE 1

A Tablet for Oral Administration Containing a Compound of Formula (I) for Stimulating Hair Growth

| Ingredient | q.ty (mg) |
| --- | --- |
| Microcrystalline cellulose | 60-120 |
| Hydroxypropylmethylcellulose K100 | 20-60 |
| 2-(2-(2-Imino-4-oxo-thiazolidin-5-yl)-acetylamino)-4,5-dimethyl-thiophene-3-carboxylic acid ethyl ester | 5-30 |
| Magnesium stearate | 5-10 |
| Silicon dioxide | 10-20 |
| Polyvinylpyrrolidone K30 | 5-10 |
| Hyaluronic acid | 0.5-2.0 |
| Polyethylene glycol | 5-10 |
| Methacrylic Acid - Methyl Methacrylate Copolymer | 10-20 |
| Triethyl Citrate | 1.5-3 |
| Polysorbate 80 | 0.5-1.0 |
| Titanium dioxide | 1.5-2.5 |
| Talc | 3-6 |

EXAMPLE 2

A Lotion for Topical Application Containing a Compound of Formula (I) for Stimulating Hair Growth

| Ingredient | q.ty (mg) |
| --- | --- |
| Aqua | 1350-1850 |
| Hydroxypropyltrimonium hyaluronate | 1.3-3.8 |
| Ethanol | 1900-2600 |
| 2-(2-(2-Imino-4-oxo-thiazolidin-5-yl)-acetylamino)-4,5-dimethyl-thiophene-3-carboxylic acid methyl ester | 0.01-1.00 |
| Lactic acid 80% | 7-10 |
| PEG-40 Hydrogenated castor oil | 35-45 |
| Octadecyl di-t-butyl-4-hydroxyhydrocinnamate | 1.5-2.0 |
| Lecithin | 1.5-2.0 |
| Fomblin HC/PU-CAT5 | 0.6-0.8 |

EXAMPLE 3

A Composition for Topical Application Containing a Compound of Formula (I) for Treating Alopecia

| Ingredient | q.ty (mg) |
| --- | --- |
| Aqua | 940-2800 |
| Ethanol | 900-1800 |
| Hydroxypropyltrimonium hyaluronate | 3-4 |
| Acetyl L-carnitine hydrochloride | 17-23 |
| Caffein | 2-3 |
| L-Arginine hydrochloride | 2-3 |
| Calcium Pantothenate | 6.5-8.5 |
| 2-(2-(2-Imino-4-oxo-thiazolidin-5-yl)-acetylamino)-4,5-dimethyl-thiophene-3-carboxylic acid methyl ester | 0.01-1.00 |
| Lactic acid 80% | 2-3 |
| Biotin | 0.5-0.8 |
| PEG-40 Hydrogenated castor oil | 700-1000 |
| Lecithin | 17-23 |
| Parfum | 2.0-2.5 |

| Ingredient | q.ty (mg) |
|---|---|
| *Ajuga Reptans* dry extract | 8.5-11.5 |
| Fomblin HC/PU-CAT5 | 0.7-1.1 |

EXAMPLE 4

Experimental Evidence

Evidence of the activity of compounds of the invention is provided by the expression of Lymphoid enhancer binding factor-1 (Lef1), which plays an important role in bulge stem cells cell growth and differentiation (International Journal of Medical Sciences 2013; 10 (6):738-746).

Test Compounds

Compounds tested were:

C1: 2-(2-(2-Imino-4-oxo-thiazolidin-5-yl)-acetylamino)-4,5-dimethyl-thiophene-3-carboxylic acid methyl ester C5: 2-(2-(2-Imino-4-oxo-thiazolidin-5-yl)-acetylamino)-4,5-dimethyl-thiophene-3-carboxylic acid ethyl ester.

These products were reconstituted in DMSO (stock solution) and intermediate or working solutions were prepared diluting the stock or the intermediate solution in William's E medium.

Hair Follicle (HF) Organ Culture

Microdissected human anagen VI scalp HFs (were cultured at 37° C. with 5% CO2 in a minimal media of William's E media (Gibco, Life Technologies) supplemented with 2 mM of L-glutamine (Gibco), 10 ng/ml hydrocortisone (Sigma-Aldrich), 10 µg/ml insulin (Sigma-Aldrich) and 1% penicillin/streptomycin mix (Gibco) to make Williams Complete Media (WCM) as previously described (Philpott et al., 1990; Kloepper et al., 2010; Langan et al., 2015). After 24 hrs, the medium was replaced with fresh medium containing either WCM containing a final concentration of 0.1% of DMSO (vehicle) or test compounds at final concentrations of 15 µM for C1 & C5. For qRT-PCT, RNA was extracted from hair follicles treated only for 6 hours.

qRT-PCR Analysis

RNA was extracted from hair follicles with RNeasy kit (Qiagen, USA), and reverse transcribed with Tetro cDNA synthesis kit (Bioline) according to manufacturer's instructions. qPCR was performed in QuantStudio3 (Thermo Fisher) with Taqman probe for Axin2 (Hs00610344_m1, Thermo Fisher), Lef1 (Hs01547250_m1, Thermo Fisher), b-actin (Hs01060665_g1, Life Technologies) and Gapdh (Hs02758991_g1, Thermo Fisher). Expression levels were calculated with the delta-delta CT method.

Results

Lef-1 (Genic Expression)

The following table reports the genic expression of Lef1 (mRNA) in follicles microsectioned treated with the vehicle, C1 and C5.

The Lef1 expression is normalized on the average of housekeeping (GAPDH). N=8 HFs/group from 1 donor.

|  | Vehicle | C1 | C5 |
|---|---|---|---|
| mean | 1 | 3.425 | 6.134 |
| SEM | 0.01 | 0.251 | 0.326 |

The expression with compounds C1 and C5 shows a 3 to 6 fold increase in respect with the one obtained by the vehicle alone.

Figure 1:
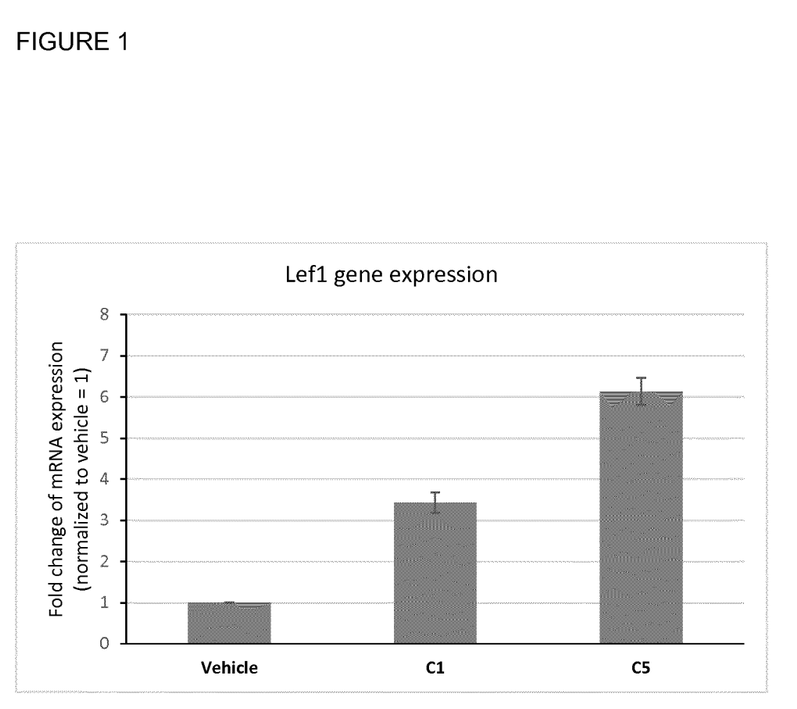
FIG. 1 shows a 3 to 6 fold increase of the Lef1 gene expression obtained by its stimulation with two compounds of the invention identified as C1 and C5 in Example 4, in respect with the one obtained by the vehicle alone.

The results are illustrated in FIG. 1.

Figure 2:
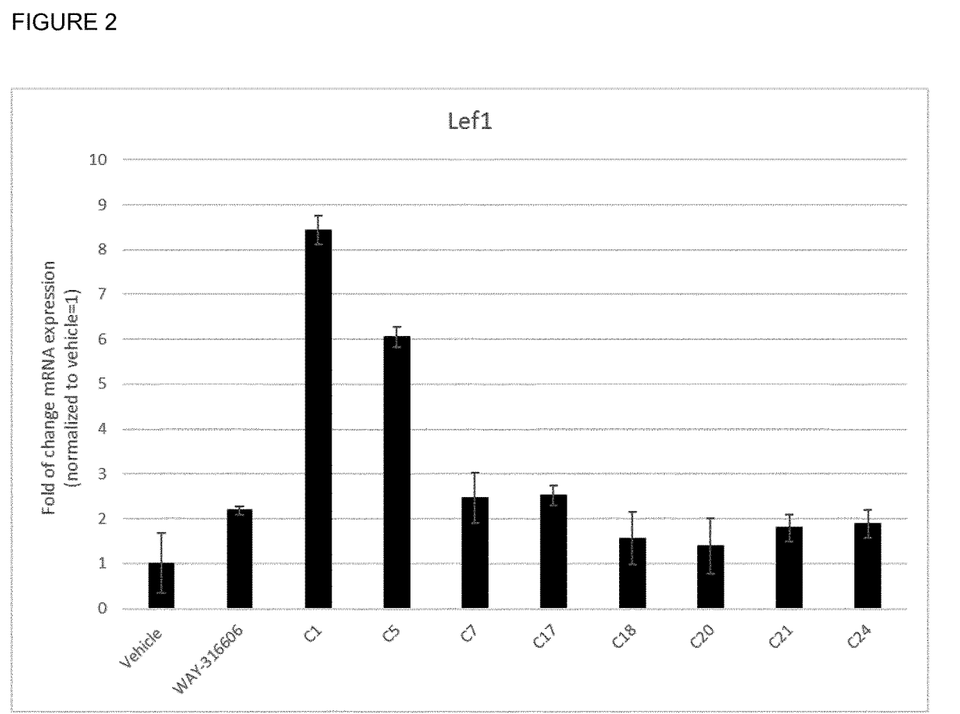
FIG. 2 shows additional tests with the aim to show the hair growth promotion activity of the iminoxothiazolidine compounds of the invention, especially those reported in the following Table I using Hair cell line (derma papilla cells).

EXAMPLE 5 (FIG. 2)

Additional tests with the aim to assess the hair growth promotion activity of the iminoxothiazolidine compounds of the invention, especially those reported in the following Table I.

In the present test, Hair cell line (derma papilla cells) were used rather than human hair follicle, as in the experiment of Example 4.

We evaluated the stimulation of Lef1 (marker of hair growth) and we retested compound 1 and compound 5 and we use also included the compound WAY-316660, a relatively non-toxic specific antagonist of SFRP1, which has already been used for the treatment of osteoporosis, for its known hair growth promotion activity (Rif. Hawkshaw et al. Plos Biol, 2018; https://journals.plos.org/plosbiology/article?id=10.1371/journal.pbio.2003705).

TABLE I

Tested compounds

| Compound | Formula |
|---|---|
| Way 316606 (positive control) |  |

TABLE I-continued

Tested compounds

| Compound | Formula |
| --- | --- |
| Compound 1 (C1)<br>2-(2-(2-Imino-4-oxo-thiazolidin-5-yl)-acetylamino)-4,5-dimethyl-thiophene-3-carboxylic acid methyl ester | (structure) |
| Compound 5 (C5)<br>(Substitution of compound 1 in $R^3$ on thiophene scaffold) | (structure) |
| Compounds 7 (C7)<br>(Substitution of compound 1 in $R^2$-$R^3$ on thiophene scaffold) | (structure) |
| Compound 17 (C17)<br>(Substitution of compound 1 in $R^1$-$R^2$ on thiophene scaffold) | (structure) |
| Compound 18 (C18)<br>(Substitution of compound 1 in $R^1$-$R^2$ on thiophene scaffold) | (structure) |
| Compound 20 (C20)<br>(Substitution of compound 1 in $R^1$-$R^3$ on thiophene scaffold) | (structure) |

TABLE I-continued

Tested compounds

| Compound | Formula |
|---|---|
| Compound 21 (C21) (Substitution of compound 1 in $R^1$(cycloalkyl group)-$R^3$ on thiophene scaffold) | [structure: ethyl ester of cyclopropyl-substituted thiophene with iminothiazolidinone-acetamide] |
| Compound 24 (C24) | [structure: primary amide of cyclobutyl-substituted thiophene with iminothiazolidinone-acetamide] |

Biological Model
Human Follicle Dermal Papilla Cells (HFDPC)

The Human Follicle Dermal Papilla Cells (HFDPC) were purchased from Promocell (Germany).

The cell line was cultured in Follicle Dermal Papilla Cell medium in 25 cm² culture flasks at 37° C., 5% CO2. Every two days confluent cultures were splitted 1:3-1:6, after washing with PBS 1× (without Ca2+ and Mg2+), using Trypsin/EDTA and seed at 2-5·10⁴ cell/cm², 37° C., 5% $CO_2$.

Freezing medium: Cryo-SFM. Cell quantification: trypan blue assay

Controls

Positive control: Way316606

Negative control: Untreated cells in Follicle Dermal Papilla Cell under the same sample cultural condition.

Methods

The expression of LEF1 was investigated by RT-PCR. The analysis was performed according to the reported method (Gibson et al, 1996; Heid et al, 1996) using TaqMan Gene Expression Assay supplied by Applied Biosystems. Briefly, within a gene-specific PCR oligonucleotide primer pair, an oligonucleotide probe labelled with a reporter fluorescent dye (FAM) at the 50-end and a quencher fluorescent dye (TAMURA) at the 30-end was designed. When the probe was intact, the reporter dye emission was quenched. During the extension phase of the PCR cycle, the nucleolytic activity of the DNA polymerase cleaved the hybridization probe and released the reporter dye from the probe. Fluorescence intensity produced during PCR amplifications was monitored by a sequence detector directly in the reaction tube ("real time"). A computer algorithm compared the amount of reporter dye emission with the quenching dye emission and calculated the threshold cycle number (CT) when signals reached ten times the standard deviation of the baseline, from which the levels of the mRNAs transcribed from the various genes tested were obtained (Gibson et al, 1996).

Gene expression analysis involves four following step:
1. Treatments of cells with active compounds for 24 h;
2. RNA extraction;
3. cDNA retro transcription;
4. Quantitative RT-PCR;

Day 1: Seed cells

When the cells (Human Follicle Dermal Papilla Cells) reached approximately 80% confluence, they were harvested with trypsin/EDTA and seeded at a density of 1×10⁶ cells/ml into 12-well plates and then incubated at 37° C., 5% $CO_2$ (24 h).

Day 2-3: Chemical Exposure 24 H

When the cells reached approximately 80% confluence, complete medium was removed; cells were washed once with PBS 1× and the incubated in Human Follicle Dermal Papilla Cells at 37° C., 5% $CO_2$ for at least 24 h;

Compounds to be tested (WAY316606, 1, 5, 7, 17, 18, 20, 21, 24) were dissolved in DMSO and diluted at final concentration in Human Follicle Dermal Papilla Cells.

Controls (medium only) were also included.

Cells were then incubated at 37° C., 5% $CO_2$ for different 24 h.

RNA Extraction

Total RNAs were extracted from the cells using Tri Reagent (Thermo Fisher), that is a single, homogenous solution for the isolation of total RNA. This procedure is an improvement of the single-step method reported by (Chomczynski and Mackey, 1995) for total RNA isolation. Tri Reagent, a mixture of guanidine thiocyanate and phenol in a monophase solution, effectively dissolves DNA, RNA, and protein on homogenization or lysis of tissue sample and contains a unique combination of denaturants and RNase inhibitors and is used in a convenient, single-step disruption/separation procedure.

The purity of total RNA extracted was assessed by reading absorbance at 260 nm, the λ at which the nucleic acid has the highest absorbance. It was also read the absorbance at 280 nm, to assess contamination by proteins or phenol. Whereas measuring the absorbance at 230 nm and 330 nm provides information about the purity of both samples and couvette. The RNA is considered of good quality if the R=A260/A280 ratio is >1.6.

After have determining the total RNA concentration and purity each sample of RNA was diluted in DEPC water to a final concentration of 2 μg/ml. This is the required concentration by the retro transcription kit (in the follow phase)

It was also performed an electrophoresis gel running to verify the integrity of the total RNA extracted.

Reverse Transcription PCR

Total RNA, extracted and quantified, was amplified using the "PRIME SCRIPT RT reagent kit (Perfect Real time) (Takara).

Random primers were used in order to ensure an efficient synthesis of the first strand of the mRNA.

For amplification we used the Real time PCR System Mx3000P (Stratagene) and each total RNA was amplified in duplicate.

| AMPLIFICATION CONDITIONS | Step 1: | Step 2: | Step 3: |
|---|---|---|---|
| Temperature | 37° C. | 85° C. | 25° C. |
| Time | 15 min | 5 sec | hold |

After amplification samples were diluted with 30 μl of DEPC water and stored at −20° C. until use.

Real Time PCR

The RT-PCR analysis was set, using TaqMan linear probes (Applied Biosystems). Those probes are the most widely used and published detection chemistry for qPCR applications.

Inventoried probes and primers were chosen according to previously specific bibliographic studies.

We have used the relative quantification method in which the relative concentration of the gene interest (target) in unknown samples is compared to a calibrator, or control sample (untreated cells). Here, the calibrator is a baseline for the expression of a given target gene. Using this approach, differences in Ct value between an unknown sample and calibrator are expressed as fold-changes relative to the calibrator sample. In addition to comparing the expression of the target gene alone in a control versus experimental sample, it is useful to normalize the results with a normalizing target, typically a gene whose expression is constant in both the control and experimental sample. GAPDH was the housekeeping gene used to normalize results. Using this type of quantification it's no necessary to run a standard curve on every plate, assessing an amplification efficiency of 100%. The TaqMan gene expression assay supplied by Applied Biosystems is optimized for the follow thermal profile and a 100% efficiency.

The Following Gene were Studied:

| GENE NAME | TAQMAN ASSAY ID | Amplification program |
|---|---|---|
| GAPDH (housekeeping) | Hs99999905_m1 | 95° C. 15 s |
| | | 60° C. 60 s |
| | | For 40 cycles |
| LEF1 | Hs01547250_m1 | 95° C. 15 s |
| | | 60° C. 60 s |
| | | For 40 cycles |

Experimental Procedure

RT-PCR was performed using the cDNAs from different time points treated cells, control cells (untreated) were added to 10 μl of 2× TaqMan Gene Expression Master Mix and 1 μl of 20× TaqMan Gene Expression assay. Each biological sample was treated in duplicate and amplified both with housekeeping TaqMan gene expression assay and target TaqMan gene expression assay. Also a non template control sample (NCT) was included in every run.

The Stratagene termocycler MX3000P was programmed as follow:

| 95° C., | 30 sec | (Amplitaq activation); |
|---|---|---|
| 95° C., | 5 sec | (Denaturation) |
| 60° C., | 20 sec | (Annealing - extension) |

| | STEP | |
|---|---|---|
| | Step 1: Activation of Taq Polymerase | Step 2: PCR Cycle (40 cycles) |
| | Hold | Denature | Anneal/Extend |
| Temperature | 95° C. | 95° C. | 60° C. |
| Time | 30 sec | 5 sec | 20 sec |

Data Collection

Data provided by Stratagene MX3000P instrument were registered by the internal software MXPro v.4.01. When amplification is complete, the software will apply automatically the $2^{-\Delta\Delta Ct}$ method calculating the Ct differences between the target gene in the treated samples and calibrator, and correct that by the difference in Cts for the normalizer gene in the treated and calibrator samples. The Ct values of the target and the normalizer should ideally be within about ten cycles of each other.

The output for a comparative quantization run is a relative quantity chart. A value of one indicates no change in target gene expression between that sample and calibrator sample. Anything greater that one indicates up-regulation and anything lower than one indicates down-regulation. A value is significantly accepted if is once up-regulated or down-regulated respect to the calibrator.

RESULTS

After 24 h of incubation all tested compounds were able to induce and stimulated LEF1 mRNA expression (FIG. 1). Also WAY316606, used as positive control exerted such inductive action.

| | Lef1 | |
|---|---|---|
| | fold of change mRNA expression | SEM |
| Vehicle | 1 | 0.668 |
| WAY-316606 | 2.18 | 0.097 |
| C1 | 8.43 | 0.314 |
| C5 | 6.05 | 0.226 |
| C7 | 2.46 | 0.559 |
| C17 | 2.52 | 0.229 |
| C18 | 1.56 | 0.592 |
| C20 | 1.39 | 0.621 |
| C21 | 1.79 | 0.299 |
| C24 | 1.88 | 0.314 |

The major induction of Lef1 was obtained with compounds 1 and 5.

After 24 h of all tested compounds were able to inhibit Lef1 mRNA expression, as illustrated in (FIG. 2). Also WAY316606, used as positive control, exerted such inhibitory action.

The invention claimed is:

1. A method for reducing hair loss in a subject, said method comprising:

administering to said subject an iminooxothiazolidine compound of formula (I)

(I)

wherein said compound of formula (I) is selected from the group consisting of:

and

2. The method according to claim 1 wherein the compound of formula (I) is selected from the group consisting of 2-(2-(2-Imino-4-oxo-thiazolidin-5-yl)-acetylamino)-4,5-dimethyl-thiophene-3-carboxylic acid methyl ester and 2-(2-(2-Imino-4-oxo-thiazolidin-5-yl)-acetylamino)-4,5-dimethyl-thiophene-3-carboxylic acid ethyl ester.

3. The method of claim 1, wherein the selected iminooxothiazolidine compound of formula (I) is administered in a composition further comprising a physiologically acceptable carrier.

4. The method according to claim 3 wherein the composition is for local or topical application or for oral administration.

5. A method for treating a hair growth disorder in a subject in need thereof, said method comprising:

administering to said subject an iminooxothiazolidine compound of formula (I)

(I)

wherein said compound of formula (I) is selected from the group consisting of:

6. The method according to claim 5 wherein the compound is selected from the group consisting of 2-(2-(2-Imino-4-oxo-thiazolidin-5-yl)-acetylamino)-4,5-dimethyl-thiophene-3-carboxylic acid methyl ester and 2-(2-(2-Imino-4-oxo-thiazolidin-5-yl)-acetylamino)-4,5-dimethyl-thiophene-3-carboxylic acid ethyl ester.

7. The method of claim 5, wherein the iminooxothiazolidine compound of formula (I) is administered in a composition further comprising a physiologically acceptable carrier.

8. The method according to claim 7 wherein the composition is for local or topical application or for oral administration.

9. The method of claim 5, wherein the hair growth disorder is alopecia, telogen effluvium, or androgenetic alopecia.

* * * * *